(12) United States Patent
Buch-Rasmussen et al.

(10) Patent No.: US 6,482,509 B2
(45) Date of Patent: *Nov. 19, 2002

(54) COATING SYSTEM PROVIDING LOW FRICTION

(75) Inventors: Thomas Buch-Rasmussen, Gentofte (DK); Patric Jannasch, Roskilde (DK); Erling Bonne Jørgensen, Veskø (DK); Ib Johannesen, Værlose (DK); Sokol Ndoni, Copenhagen (DK); Nils Berg Madsen, Ølsykke (DK)

(73) Assignee: Novo Nordisk A/S, Bagsvaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 48 days.

(21) Appl. No.: 09/260,757

(22) Filed: Mar. 2, 1999

(65) Prior Publication Data

US 2002/0037401 A1 Mar. 28, 2002

Related U.S. Application Data (60) Provisional application No. 60/087,471, filed on Jun. 1, 1998.

(30) Foreign Application Priority Data

Mar. 6, 1998 (DK) .......................................... 1998 0314

(51) Int. Cl.[7] .......................... B32B 17/06; B32B 15/04
(52) U.S. Cl. ...................... 428/336; 428/429; 428/447; 428/450; 428/451; 604/12; 604/230
(58) Field of Search ................................ 428/447, 336, 428/429, 450, 451; 604/12, 230

(56) References Cited

U.S. PATENT DOCUMENTS

| | | | |
|---|---|---|---|
| 4,767,414 A | 8/1988 | Williams et al. | 604/230 |
| 4,844,986 A | 7/1989 | Karakelle et al. | 428/447 |
| 5,338,312 A | 8/1994 | Montgomery | 604/230 |

FOREIGN PATENT DOCUMENTS

AU          603862          8/1989

OTHER PUBLICATIONS

JP 9324171 (Nippon Sheet Glass Co. Ltd.), Dec. 16, 1997.

*Primary Examiner*—D. S. Nakarani
(74) *Attorney, Agent, or Firm*—Skadden, Arps, Slate Meagher & Flom LLP (57) ABSTRACT

The present invention relates to a coating system, in particular to a coating system for articles where plastic materials slide against flexible rubber materials. The coating system is a silicone oil based coating having a viscosity of at least 200,000 centistokes, i.e. a high viscosity coating. The coating comprises in a preferred embodiment a silicone oil based block or graft copolymer, or segmented copolymer. Further the invention relates to a process of producing a component of an article coated as described above, comprising adding the coating material to the component material prior to molding and subsequently molding the component from the mixture, or molding the component from the component material and subsequently applying the coating material to the at least one surface of the component, as well as an article coated with a silicone oil based coating as defined above. Such an article is preferably a medical article, such as a container or an injection cylinder and a stopper. The coatings according to the present invention are especially suited to use for permanently coating internal surfaces of containers equipped with stoppers for storage and administration of liquid protein preparations. The coatings providing low friction between the two components, such as a container wall and a rubber stopper, result in high-precision dosing. The described coatings are particularly useful for coating containers for storage and administration of liquid protein solutions, such as insulin formulations.

20 Claims, 3 Drawing Sheets

COATING SYSTEM PROVIDING LOW FRICTION

CROSS-REFERENCE TO RELATED APPLICATIONS

This application claims priority under 35 U.S.C. 119 of Danish application PA 1998 0314 filed Mar. 6, 1999 and U.S. Provisional application 60/087,471 filed Jun. 1, 1998, the contents of which are fully incorporated herein by reference.

The present invention relates to a coating system, in particular to a coating system for articles where plastic materials slide against flexible rubber materials.

The described coatings are particularly useful for coating containers for storage and administration of liquid protein solutions, such as insulin formulations.

BACKGROUND

Medical articles for dosing medical preparations, such as containers equipped with stoppers or plungers, require a smooth sliding movement of one component, e. g. a stopper, in contact with another component, e. g. a container wall, to provide reliable dosages with high precision. Often, surfaces of the components have been shown to develop an initial resistance to movement after being in contact for some time, and movement does not start until a certain applied force, hereafter called a static friction force, has been applied. The phenomenon causes a sudden, rapid relative movement of the two surfaces. Frequently, the movement stops and another resistance is built up. This kind of movement is generally known as the 'slip-stick' phenomenon and causes a problem in that it leads to irregular and imprecise dosages. The phenomenon is especially troublesome in dispensing devices where very small, dropwise dosages of protein solutions, e. g. insulin formulations, are required. If the 'slip-stick' phenomenon does not occur when the surfaces start to slide after the static friction force has been applied, the surfaces slide at a smoother rate by application of a so-called dynamic friction force.

Today large amounts of insulin are sold in dispensing devices. The insulin is filled in glass containers, which are equipped with rubber stoppers, and these containers are then loaded into dispensing devices. Usually, both the glass containers and the rubber stoppers are coated with silicone oil, poly(dimethyl siloxane) (PDMS), to reduce the friction between the container wall and the stopper. One common method to coat glass containers with silicone oil is to apply a PDMS-in-water emulsion and subsequently evaporate the water in an oven.

After the surfaces have been coated with for example a silicone oil and the plunger has been fitted to the container, the static friction force is relatively low. However, especially the static friction gradually increases with time to reach a plateau value, after which there is no further significant increase in the static friction. The time after which this plateau is reached depends on the specific system, often within a few hours. The reason for the increase in friction forces with the time elapsed after fitting the plunger in the container, is believed to be displacement of the silicone oils from the contacting surfaces by the squeezing force between the plunger and the container. The increase may also partly be due to a small absorption of the silicone oil by the rubber material.

It is an object of the present invention to provide a coating system providing a reduced friction at surfaces being in frictional engagement with each other which coating system is not displaced by the squeezing forces mentioned above. Furthermore, the present system is particular suitable for plastic/rubber combinations.

SUMMARY OF THE INVENTION

The object of the invention is obtained by a coating system for articles having at least a first component and a second component, said second component being in frictional engagement with said first component, wherein at least a part of the surface of the first or the second component is coated with a silicone oil based coating having a viscosity of at least 200,000 centistokes, i.e. a high viscosity coating.

Another object of the invention is a coating which is solid or almost solid comprising a silicone oil based block or graft copolymer, or segmented copolymer.

The coatings according to the present invention are especially suited to use for permanently coating internal surfaces of containers equipped with stoppers for storage and administration of liquid protein preparations. The coatings providing low friction between the two components, such as a container wall and a rubber stopper, result in high-precision dosing.

Another object of the invention is a process of producing a component of an article coated as described above, comprising
  adding the coating material to the component material prior to molding and subsequently molding the component from the mixture, or
  molding the component from the component material and subsequently applying the coating material to the at least one surface of the component.

A third object of the present invention is an article having at least a first component and a second component, said second component being in frictional engagement with said first component, wherein at least a part of the surface of the first or the second component is coated with a silicone oil based coating as defined above. Such an article is preferably a medical article, such as a container or an injection cylinder and a stopper.

DETAILED DESCRIPTION OF THE INVENTION

The object of the present invention is to provide a coating system whereby the friction forces between at least two components being in frictional engagement with each other is reduced. Furthermore, it is of importance that the coating system is not displaced by the squeezing forces between the two components during storing where the two components are in fluid tight engagement.

This object is achieved by the inventive coating system which comprises a silicone oil based coating having a viscosity of at least 200,000 centistokes, preferably at least 500,000 centistokes, more preferably at least 750,000 centistokes. Thus, the coating resists the squeezing forces due to the high viscosity.

The silicone oil of which the coating system is based is preferably a poly(dialkyl siloxane) oil. In a more preferred embodiment the poly(dialkyl siloxane) oil is selected from a poly(dimethyl siloxane), poly(dipropyl siloxane) oil and poly(dihexyl siloxane) oil.

To obtain the coating having a viscosity of at least 200,000 centistokes when applied to the component in question either the starting material is highly viscous, such as a highly viscous silicone oil, or the coating is treated either prior to or after being applied to the component in order to obtain the high viscosity.

The silicone oil may be of any kind, such as a linear or branched silicone oil which is cross-linkable, e.g., having reactive and/or functional chemical groups enabling cross-linking of the oil. By cross-linking, the viscosity is increased, often to infinitely great, in that the coating comprising the cross-linked silicone oil appears as a solid.

A partly cross-linked, gelled, or cured silicone oil is typically obtained by applying a linear, or branched, silicone oil with reactive functionalities which are used in cross-linking the coating in a subsequent step. There are a number of different suitable curing methods, e.g., curing by irradiation with ultraviolet light, curing in an oven at elevated temperature, and curing in the presence of water. Preferably, the cross-linkable silicone oil is of medical grade, e.g., MDX4-4159 fluid®, supplied by Dow Corning.

A cross-linked silicone oil may also be obtained by first applying a silicone oil, linear or branched, on the surface, and secondly irradiating the oil by a high-energy radiation source, e.g., an electron, x-ray, or γ-ray source. Cross-linking may also be obtained by treatment of the silicone oil in an ionizing plasma, e.g., an oxygen plasma.

It is especially advantageous to coat the surfaces with a mixture of a crosslinkable oil and a non-crosslinkable oil, or to only cure the former oil partially. In a subsequent step, the crosslinkable oil is cured. This procedure provides large opportunities to vary the degree of crosslinking.

The cross-linked oil secures the high viscosity thereby resisting the squeezing forces from the components. The non-crosslinked oil is believed to be located in between the cross-links. When the two components are in frictional engagement the non-crosslinked oil is believed to be forced to the surface thereby lubricating the surface of the coating providing a low friction coating.

The same feature is obtained by a coating comprising a cross-linkable oil alone, but wherein during the cross-linking process, only a part of the cross-linkable oil is cross-linked leaving some "free oil" between the cross-links. In the present context the term "free oil" means oil which is not cross-linked.

Another embodiment of a silicone oil based coating having the high viscosity is providing a coating comprising a block copolymer, which copolymer is based on silicone oil. Mostly, a coating comprising a block copolymer will appear as a solid on the coated component.

The block copolymers based on silicone oil can be of any kind, e. g. diblocks, triblocks, and multiblocks. Preferably the silicone oil is a poly(dialkyl siloxane), such as poly (dimethyl siloxane) (PDMS).

The silicone oil block can be combined with a polyolefinic, or a polystyrene block, or any other suitable block copolymer to form a useful block copolymer. By preparing block copolymers with high molecular weights, the viscosity can be kept high, which avoids displacement of the copolymer between the rubber material and the plastic material.

The structure of the copolymer according to the invention must be predominantly laminar as opposed to micellar. It is believed that the lubricating effect of the copolymer is due to various laminas of the copolymer sliding in relation to each other. The molecular weight of the blocks of the copolymer is among other parameters responsible for the ability of the copolymer of forming laminas instead of micelles. A too low molecular weight will cause the copolymer to form micelles and not laminas in the coating.

The molecular weight of the silicone oil blocks in the copolymer is at least 1,000, such as 10,000 g/mole, preferably at least 30,000 g/mole, more preferably at least 50,000 g/mole, most preferably at least 100,000 g/mole.

The block copolymer should be prepared and applied as a coating so that the silicone oil blocks completely cover the outermost surface of the coating to give the lowest possible friction.

One advantage of block copolymer coatings is that no curing is necessary. Further, potential leaks can be minimized by choosing block copolymers which are non-soluble in the surrounding liquid, and which are solid, or have a very high viscosity.

Yet another advantage can be reached if the silicone oil block copolymers are compatible, miscible, or at least partly miscible with the plastic and/or rubber materials used in the coated component. By blending the silicone oil block copolymers with either the rubbery material, or the plastic material, or both materials, the block copolymer can be integrated with the respective material. In this way, potential leak, or loss, of the coating material during the sliding movements can be minimized. The silicone block copolymer may be blended into the rubbery material, or the plastic material either in a separate operation, or in the forming operating in which the materials are given their final shape.

The present inventors have found that the coating system according to the invention comprising a cross-linked oil or a copolymer of high molecular weight, such as about 100,000 g/mole should be applied to either the first component or the second component but not to both components in order to achieve the low static and dynamic friction forces. The other component not being coated with the high viscosity coating described above may be un-coated. Coating systems comprising low molecular weight copolymers corresponding to non-crosslinked oils may be applied to all components without impairing the friction advantages obtained by the system.

In another embodiment the other component is coated with a coating comprising a linear or branched oil or a lightly cross-linked oil. Preferably, the oil is a silicone oil as described above. The viscosity of the coating on the other component is not critical, but may be adjusted to the high viscosity coating. Mostly, the viscosity of the coating on the other component is much lower than for the high viscosity coating.

The coating systems described above are especially suited to use for permanently coating internal surfaces of plastic containers and rubber plungers in devices for storage and administration of liquid protein solutions. The coatings provide very low friction between the container wall and the rubber plunger. Specifically, the coatings enable that the sliding movement starts and is maintained by application of the low static and low dynamic friction forces necessary to obtain high-precision dosages.

The coating system is very well suited for coating plastic components. In particular the coatings comprising a block copolymer are suitable plastic coatings in that one block may be made compatible with the plastic material of the component to be coated. Furthermore, the copolymer may be integrated with the plastic material preventing leak from the content of the plastic material.

The thickness of the coating depends on the specific coating, and is preferably from 0.005 to 10 µm, more preferably from 0.01 to 1 µm. The optimal thickness depends on the dimensions and shape of the components, and it can easily be performed by one skilled in the art. If the coating is too thin the coating may be torn in use, thereby increasing the friction between the two components. Furthermore, if the coating is too thin difficulties arise when applying the coating in that it may be applied in an uneven layer, maybe leaving some areas of the component non-coated.

When the thickness of the coating has reached a certain plateau value the friction forces are approximately constant even when the thickness is further increased. For any coating composition the coating is preferably as thin as possible to reduce the costs. The thin coating is preferably from 0.005 to 0.4 µm, such as from 0.015 to 0.25 µm, more preferably approximately 0.2 µm.

The article coated according to the present invention is preferably a medical article, such as a drug delivery article, in particular a container as depicted in FIG. 1 for storing and administrating (injecting) a liquid medicament, such as a liquid protein solution.

Figure 1A:
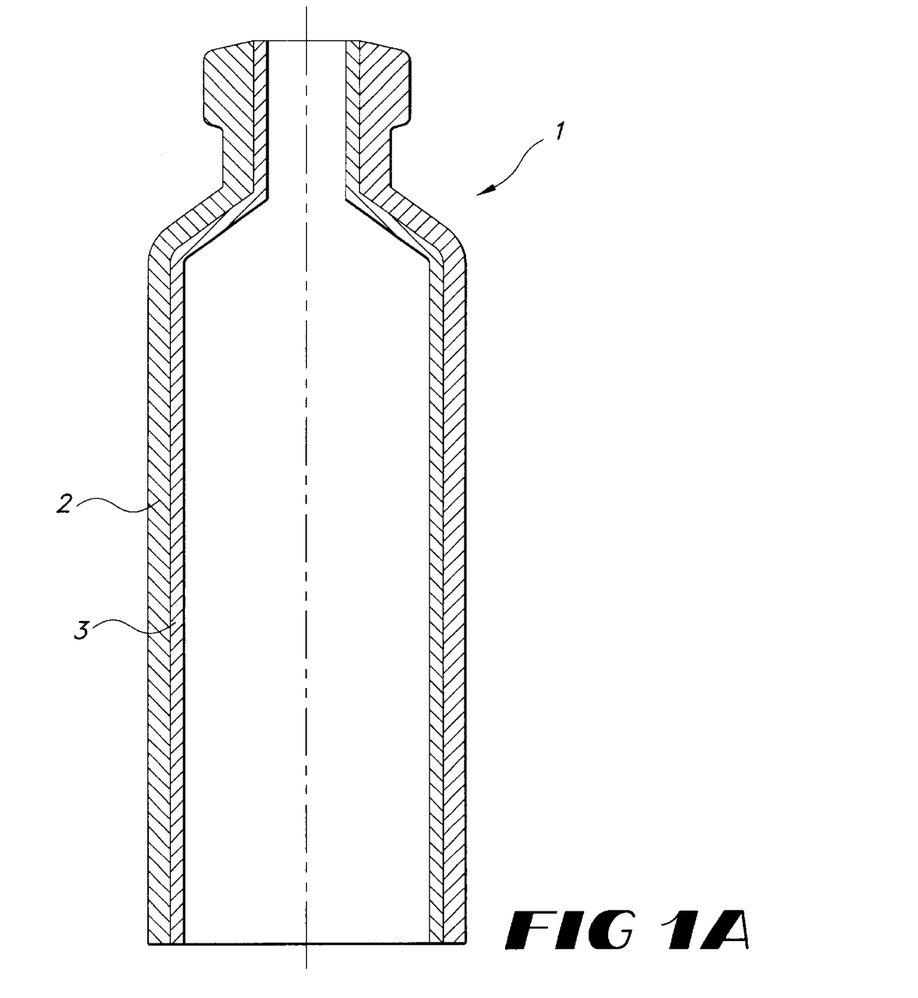
FIG. 1 shows an example of the first (FIG. 1A, injection cylinder) and second (FIG. 1B, plunger) components according to the invention. The first component is shown in longitudinal cross section. The inner diameter of the first component is 9.23 mm and the outer diameter is 11.0 mm. The outer diameter taken along line D of the second component is 9.6 mm.

In FIG. 1A an injection cylinder 1 is depicted comprising the cylinder wall 2 and a coating 3 on the inner surface of the cylinder wall 2.

Figure 1B:
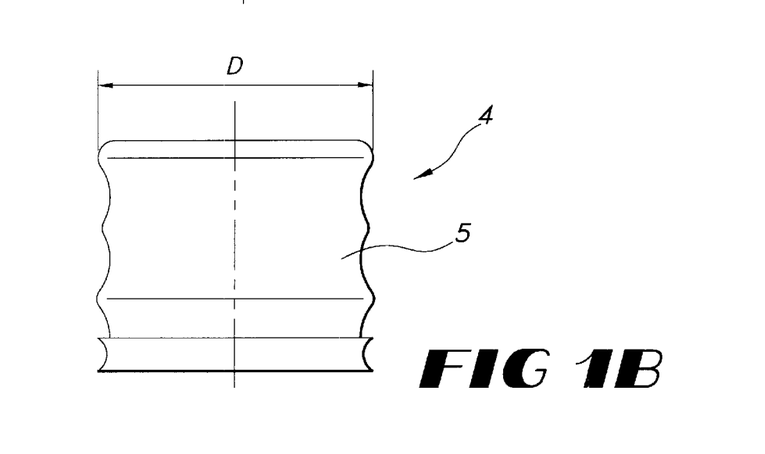
Figure 2A:
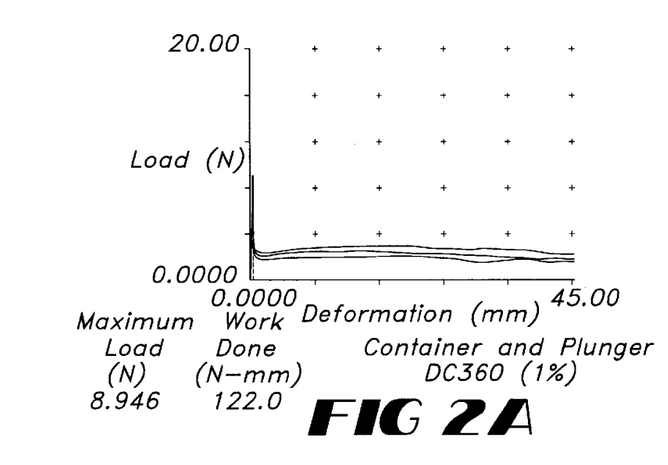
FIGS. 2A–D and FIGS. 3A–D show the results of recordings of friction forces according to Example 3 where the maximum static and dynamic friction forces are indicated as (S) and (D), respectively.
Figure 2B:
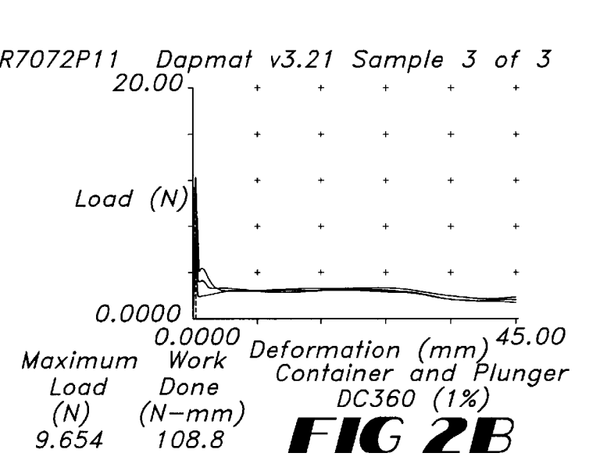
Figure 2C:
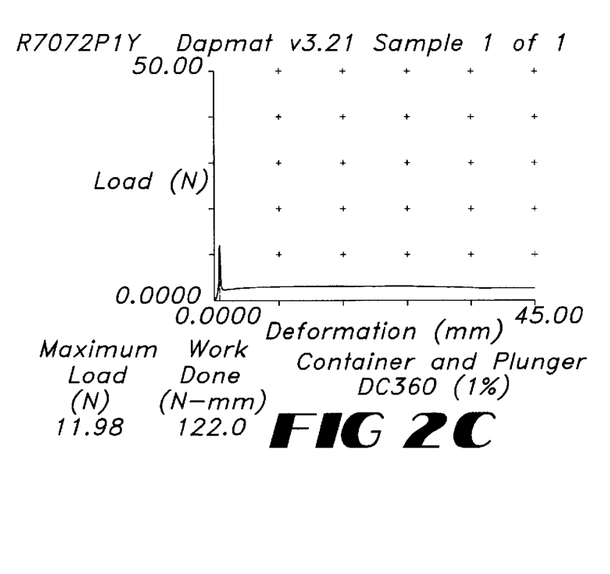
Figure 2D:
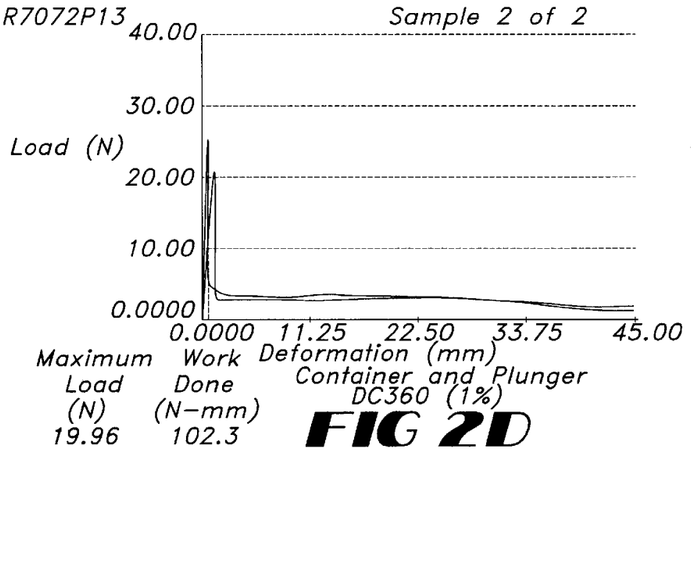
Figure 3A:
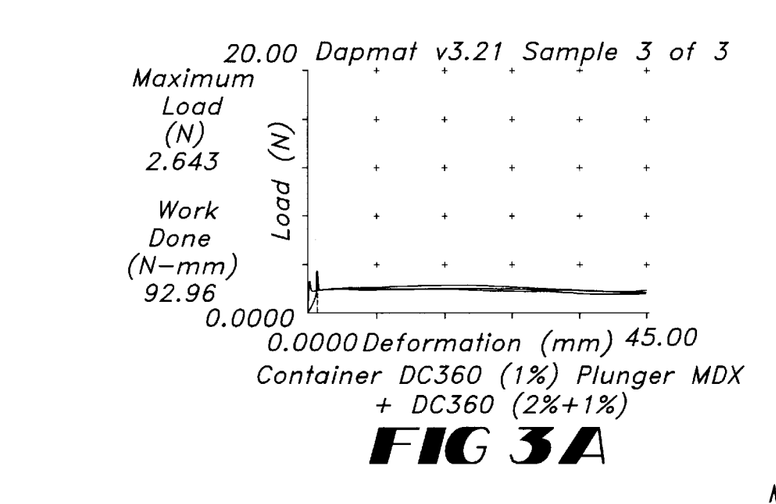
Figures 3B, 3D:
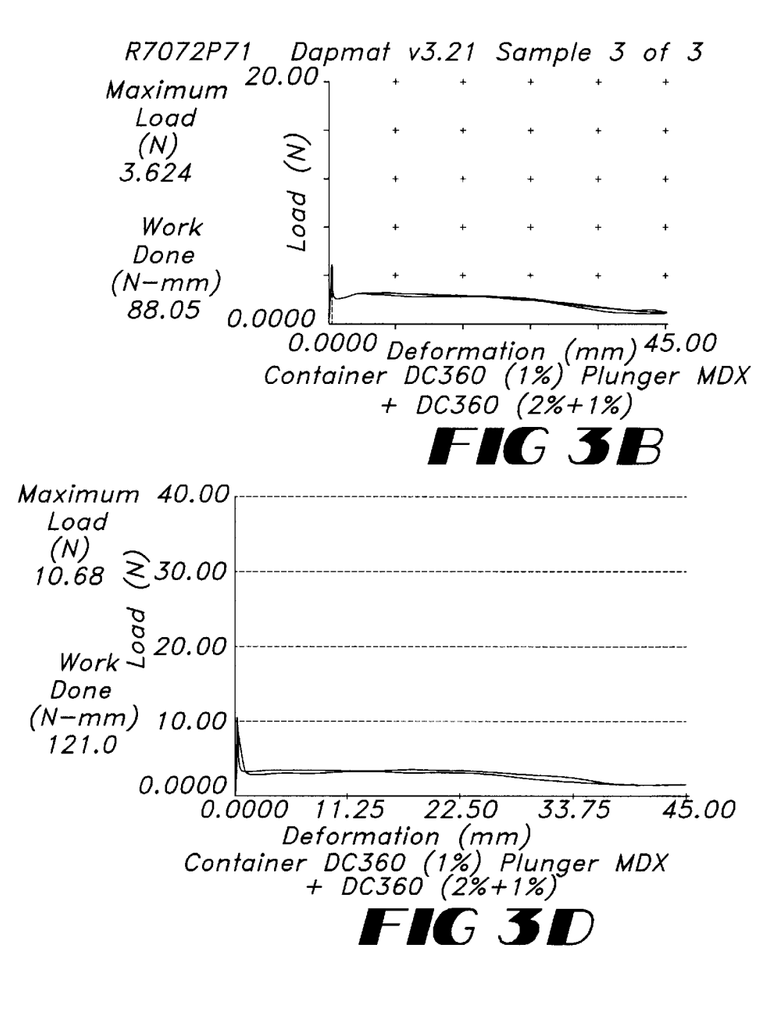
Figure 3C:
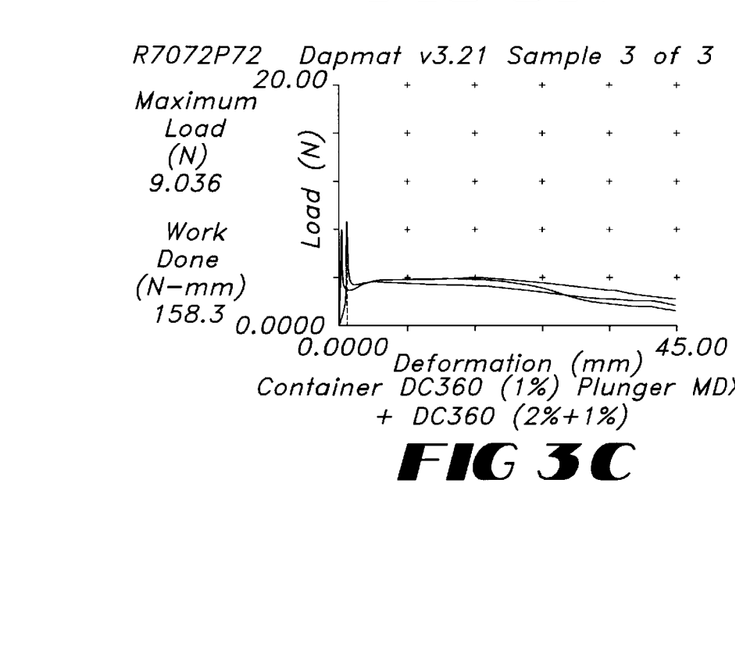

In FIG. 1B the stopper 4 is depicted with a rubber end 5 to be inserted in the injection cylinder 1. The diameter of the stopper along line D is slightly greater than the inner diameter of the injection cylinder to obtain a sufficient liquid tight sliding engagement.

The first component of the coated article is preferably a container, such as a cartridge or injection cylinder made of a material selected from glass, ceramic, metal and preferably plastic. In case of a container made of plastic, the plastic may be filled with inorganic or organic filler. The plastic material is preferably an excellent barrier against the contents of a protein solution, e. g. water and preservatives. Several different such plastic materials are commercially available, e. g. polypropylene, cyclic polyolefins, polyester resin.

The second component of the coated article is preferably a stopper at least partly made of a flexible material, such as for example a stopper made of any appropriate material with only the contacting surfaces made of a flexible material, such as rubber. An example of the latter is a stopper with an O-ring made of rubber. The stopper may also be made totally of a flexible material, such as rubber. Several suitable rubber materials are available on the market, such as bromobutyl, Santoprene®, and Trefsin®. In the present context the term stopper is used synonymously with the term plunger.

The article may further comprise mixing means. It is preferred that the surface of the mixing means is at least partly coated with a coating as defined above.

The article is preferably constructed to avoid leakage of the liquid protein formulation, in particular without leakage between the stopper and the container wall. This is a problem in particular encountered with a container for storing and administrating (injecting) the formulation because the container is filled with the formulation and stored for a longer period before use. Accordingly, the pressure of the stopper against the container wall is adjusted to withstand leakage.

The static friction force between the first component and the second component increases gradually with the storage time from the moment of frictional engagement of the two components to reach a plateau value. The plateau value is reached after some hours to several days depending on the selected coating. However, approximately 14 days after assembling of the components the plateau value has been reached for almost all coatings, and thereafter the static friction force is approximately constant. Accordingly, the static friction force measured 14 days after assembling the two components, such as placing a stopper in a container, can be taken as a measure of the long-term static friction force.

In an article coated according to the invention the long-term static friction force is below 14 N, preferably below 12 N, more preferably below 8 N, most preferably below 6 N.

Every time the movement of the two components stop the static friction forces start to build up again, approaching the plateau value. For a medical multi-dose article for injecting a drug solution this means that after each dosing of the drug the static friction forces are build up again.

The dynamic friction force should preferably be as close to the static friction force as possible to secure an even movement of the second component relative to the first component during an injection. In a preferred embodiment the dynamic friction force is below 12 N, such as 8 N, more preferably below 6 N, most preferably below 4 N.

The long-term static friction force as well as the dynamic friction force depend on the dimensions of the two components. In the present context the long-term static friction force is measured with a container as depicted in FIG. 1.

The two components are dimensioned to obtain a liquid tight sliding engagement which is the compromise between on one hand eliminating the risk of leakage between the two components and on the other hand to reduce the pressure of the two components against each other in order to reduce the friction.

Another aspect of the present invention is a process of producing a component coated as described above said process comprises adding the coating material to the component material prior to molding and subsequently molding the component from the mixture, or molding the component from the component material and subsequently applying the coating material to the at least one surface of the component.

In one embodiment the coating is applied to the component after the molding of said component. The coating may be applied by any appropriate method, such as dip coating, e. g. by dipping the material surfaces directly in the coating material, or in a solution or emulsion of the coating material, or spray coating, wherein the surfaces are sprayed with an emulsion or solution of the coating material, or by plasma polymerisation.

When applying the coating as a solution or emulsion of the coating the solvent or emulsion medium is removed after application, e.g., by evaporation.

Another embodiment is molding a component from a mixture of the coating material and the component material, whereby the coating material seeks for the surface of the component constituting a coating.

The present invention is further discussed below in Examples.

EXAMPLES

Materials. Polypropylene (PP) or cycloolefin copolymer (COC) containers, depicted in FIG. 1, with a volume of 3.5 ml and an internal diameter of 9.23 mm, were used in the evaluation of the different coatings unless stated otherwise. Polypropylene (PP) and cycloolefin copolymer (COC) and bromobutyl rubber represent[s] model materials for the container and plunger, respectively, in the examples below. The silicone oils used were Dow Coming DC360 fluid® (DC360), a non-cross-linkable oil, and Dow Corning MDX4-4159 fluids (MDX), a cross-linkable oil. The molecular data of the polystyrene-polydimethylsiloxane (PSPDMS) block copolymers which were used are shown in Table 1 below. These copolymers can be prepared by well known methods by one skilled in the art, such as described in "Order, disorder, and composition fluctuation effects in low molar mass hydrocarbonpoly-(dimethylsiloxane) diblock copolymers," Almdal, K.; Mortensen, K.; Ryan, A. J.; Bates, F. S. Macromolecules, 1996, Vol. 29 Nr. 18, p. 5940–5947. ISSN 0024-9297. The DC360 has a viscosity of 12,500 centistokes when applied to the component. MDX is cross-linked to obtain a solid coating.

TABLE 1

| Block copolymer designation | Molecular weight of the PDMS Block (kg/mol) | Molecular weight of the PS block (kg/mol) | PDMS content of the copolymer (wt %) |
| --- | --- | --- | --- |
| PSPDMS-4 | 25 | 25 | 50 |
| PSPDMS-5 | 250 | 250 | 50 |
| PSPDMS-6 | 50 | 100 | 57 |
| PEEPDMS-4 | 7 | 7 | 50 |

Coating procedure. PP containers and rubber plungers were coated with silicone oil (MDX and DC360) by a dip coating method. The containers were dip coated in heptane solutions of the silicone oils, and the rubber plungers were dip coated in a Dow Corning OS10® fluid solution of the silicone oils. PP containers were also dip coated in chloroform solutions of polystyrene-polydimethylsiloxane (PSPDMS) block copolymers. The dip coated samples were left to dry in air at ambient temperature. Further details of the coating procedures are given in the individual examples below.

Curing Procedure. Coatings containing MDX were cured by storing the coated containers in an oven at 40° C. for 10 days. A cup of water was placed in the oven to maintain a relative humidity above 30% during the curing.

Friction measurements. After coating, drying, and in some cases curing, the plungers and the containers were assembled. The containers were filled with a commercial liquid insulin solution (Actrapid® from Novo Nordisk A/S), sealed with aluminum caps, and stored for a specified time at 37° C. After the storage period, the aluminum caps were removed and the dynamic and static friction forces between the plungers and the containers were evaluated by using a Lloyds tensile tester at a constant displacement speed of 100 mm/min. The plunger was pushed down through the container by the tensile tester, and the required force was recorded as a function of the displacement. The maximum static friction force was taken as the peak friction force reached shortly after the plunger begins to move, and the maximum dynamic friction force was taken as the maximum friction force reached after the maximum static friction force had been recorded. Two recordings of friction forces are shown in FIG. 2, where the maximum static and dynamic friction forces are indicated.

The friction data given after '0 days' storage were recorded less than 30 min. after the plungers and containers were assembled. The average values of three individual measurements are reported in the examples below.

Example 1
Influence of the Location and Types of Coatings on the Friction Properties The plungers and the containers were dip coated in solutions of DC360, MDX, and a mixture of DC360 and MDX, as shown below in Table 2.

TABLE 2

| Coating on container* | Coating on plunger* | Maximum static friction force after 0 and 14 days (N) | Maximum dynamic friction force after 0 and 14 days (N) |
| --- | --- | --- | --- |
| DC360 (1%) | — | 6; 15 | 4; 4 |
| — | MDX (1%) | 6; 15 | 6–16; 15 |
| DC360 (1%) | MDX (1%) | 3; 9 | 2; 4 |
| DC360 (1%) | MDX + DC360 (1% + 1%) | 3; 7 | 3; 3 |
| MDX (1%) | MDX + DC360 (1% + 1%) | 7; 16 | 6; 5 |
| MDX + DC360 (1% + 1%) | MDX + DC360 (1% + 1%) | 7; 17 | 5; 5 |

*Numbers in parentheses give the concentrations of the oils in the dip coating solution The results show that systems coated with only a single coating of DC360 or MDX gave a high static friction with time. By applying a combination of DC360 on the container and MDX or a mixture of MDX and DC360 on the plunger, both the static and dynamic friction forces could be greatly reduced. Applying combinations of MDX (a high viscosity coating) on both the plunger and container gave unacceptable higher friction forces.

Example 2
Influence of Concentration and Composition of the Coatings on the Friction Properties By changing the concentrations of the silicone oils in the dip coating solutions, the thickness of the coatings can be varied, i. e. an increased concentration gives a thicker coating. The plungers and the containers were dip coated in solutions of DC360, MDX, and a mixture of DC360 and MDX, having different concentrations, as shown below in Table 3.

TABLE 3

| Coating on container* | Coating on plunger* | Maximum Static friction force after 0 and 14 days (N) | Maximum dynamic friction force after 0 and 14 days (N) |
| --- | --- | --- | --- |
| DC360 (1%) | MDX + DC360 (1% + 0.3%) | 3; 9 | 3; 3 |
| DC360 (1%) | MDX + DC360 (1% + 1%) | 3; 7 | 3; 3 |
| DC360 (1%) | MDX + DC360 (1% + 5%) | 3; 7 | 4; 3 |
| DC360 (0.5%) | MDX + DC360 (1% + 1%) | 4; 8 | 4; 4 |

Numbers in parentheses give the concentrations of the oils in the dip coating solution The results show that by increasing the concentration of DC360, from 0.3% to 1%, in the MDX/DC360 solution employed to coat the plungers, the static friction after 14 days could be decreased. However, no further reduction in the static friction after 14 days was noticed after increasing the concentration of DC360 from 1% up to 5%. Reducing the concentration of DC360 in the dip coating solution for the containers, from 1% to 0.5%, gave a slightly higher yet still acceptable static friction force.

Example 3

Influence of the Storage Time on the Friction Properties

PP containers were stored for 0, 7, 14, and 91 days before evaluating the friction properties. The plungers and the containers were dip coated in solutions of DC360, MDX, and a mixture of DC360 and MDX, as shown below in Table 4.

TABLE 4

| Coating on container* | Coating on plunger* | Maximum static friction force after 0, 7, 14 and 91 days (N) | Maximum dynamic friction force after 0, 7, 14, and 91 days (N) |
|---|---|---|---|
| DC360 (1%) | DC360 (1%) | 7; 11; 20; 22 | 4; 4; 4; 4 |
| DC360 (1%) | MDX (1%) | 2; 4; 7; 9 | 2; 3; 4; 4 |
| DC360 (1%) | MDX + DC360 (1% + 1%) | 3; 3; 4; 8 | 2; 3; 4; 4 |
| DC360 (1%) | MDX + DC360 (2% + 1%) | 3; 4; 9; 10 | 3; 3; 4; 4 |

*Numbers in parentheses give the concentrations of the oils in the dip coating solution FIGS. 2A–2D show the friction forces for a container and plunger both coated with DC360 (1%), and FIGS. 3A–3D show the friction forces for a container coated with DC360 (1%) and a plunger coated with MDX+DC360 (2%+1%).

The results show that the static friction increased gradually with the storage time to approach a plateau value. The increase in the dynamic friction was more moderate and much lower values were reached, as compared to the static friction. As shown in Example 1, the combination of DC360 on the container surfaces and a mixture of MDX and DC360 on the plungers proved to give the lowest levels of static friction forces. Applying a thick coating with a high content of MDX (2% MDX+1% DC360) (FIG. 3) on the plungers gave slightly higher friction forces, which is probably due to the physical barrier that a thicker coating is when the plunger is moved.

Example 4

Influence of Container Diameter on the Friction Properties

PP containers with inner diameters of 9.23 and 9.44 mm were used in this example. The plungers and the containers were dip coated in solutions of DC360, and a mixture of DC360 and MDX, respectively.

TABLE 5

| Coating on Container* | Container Inner Diameter (mm) | Coating on Plunger* | Maximum Static Friction Force after 0, 1, 7, 14, and 70 days (N) | Maximum Dynamic Friction Force after 0, 1, 7, 14, and 70 days (N) |
|---|---|---|---|---|
| DC360 (1%) | 9.23 | MDX + DC360 (1% + 1%) | 2; 6; 8; 9; 10 | 3; 3; 3; 3; 3 |
| DC360 (1%) | 9.44 | MDX + DC360 (1% + 1%) | 2; 4; 5; 5; 6 | 2; 2; 2; 2; 2 |

*Numbers in parentheses give the concentrations of the oils in the dip coating solution By increasing the inner diameter of the container, the pressure applied by the plunger on the container surface is reduced, and the friction forces are reduced accordingly.

By increasing the container diameter by 2.5%, the static friction force and the dynamic friction force were reduced by 40 and 30%, respectively. However, by reducing the pressure between the container wall and plunger increases the risk of leakage of fluid. The same effect can also be achieved if the diameter of the plunger is decreased.

Example 5

Influence of Different Block Copolymers Based on Silicone Oil (PDMS) on the Friction Properties The PP containers were dip coated in 0.5 wt% chloroform solutions of polystyrene-polydimethylsiloxane (PSPDMS) block copolymers.

TABLE 6

| Coating on container | Dip coating speed (mm/s) | Coating on plunger* | Maximum static friction force after 10 and 21 days (N) | Maximum dynamic friction force after 10 and 21 days (N) |
|---|---|---|---|---|
| PSPDMS-6 | 1 | DC360 (1%) | 11; 12 | 14; 14 |
| PSPDMS-6 | 4 | DC360 (1%) | 7; 8 | 6; 7 |
| PSPDMS-4 | 1 | DC360 (1%) | 10; 14 | >20; >20 |
| PSPDMS-5 | 1 | DC360 (1%) | 8; 12 | 9; 11 |

*Numbers in parentheses give the concentrations of DC360 in the dip coating solution The data in Table 6 show low static and dynamic friction forces except for the coating comprising PSPDMS-4. This is believed to be due to the low molecular weight of the blocks maybe causing the copolymer to form micelles instead of laminas. This phenomenon will cause a higher dynamic friction in that the micelles will not slide in relation to each other as will the laminas.

A higher dip coating speed, giving a thicker coating, during coating with PSPDMS-6 significantly reduced the friction forces.

Example 6

Influence of the Thickness of the Block Copolymer Coatings on the Friction Properties The PP containers were dip coated in chloroform solutions of the PSPDMS-5 block copolymer. By changing the concentrations of the copolymer in the dip coating solutions and the dip speed, the thickness of the coatings was varied, i. e. an increased concentration and increased dip speed give thicker coatings.

TABLE 7

| Coating on container | Copolymer concentration in dip coating solution (wt %) | Dip coating speed (mm/s) | Coating on plunger* | Maximum static friction force after 7 and 14 days (N) | Maximum dynamic friction force after 7 and 14 days (N) |
|---|---|---|---|---|---|
| PSPDMS-5 | 0.5 | 4 | DC360 (1%) | 7; 7 | 6; 6 |
| PSPDMS-5 | 1.0 | 4 | DC360 (1%) | 7; 7 | 6; 6 |
| PSPDMS-5 | 1.0 | 2 | DC360 (1%) | 7; 7 | 6; 6 |
| PSPDMS-5 | 1.0 | 1 | DC360 (1%) | 7; 7 | 6; 7 |
| PSPDMS-5 | 1.0 | 2 | — | 7; 8 | 5; 6 |

*Numbers in parentheses give the concentrations of DC360 in the dip coating solution The results shows that there is no significant influence of the coating thickness on the friction properties in the studied region. It seems as the thickness of the coating can be reduced further without any increase in friction forces. As described above, when the thickness has reached a plateau value the friction forces will not decrease by increasing the thickness.

Also interesting is that there was only a minor increase in the friction forces if the DC360 coating was removed from the plunger, thus only the container needed to be coated in order to reach low friction values.

Example 7
Influence of Polyolefin-PDMS Block Copolymer Coatings on the Friction Properties Cycloolefin copolymer (COC), TOPAS 6013, containers were dip 1% wt. solution of PEEPDMS-4 in OS10®. The bromobutyl plungers were washed in OS10®. Half of the plungers were dip in the 1% wt. solution of PEEPDMS-4.

TABLE 8

| Coating on container | Container diameter | Coating on plunger | Maximum static friction force after 0 and 7 days (N) | Maximum dynamic friction force after 0 and 7 days (N) |
|---|---|---|---|---|
| PEEPDMS-4 | 9.35 | — | 3; 8 | 3; 3 |
| PEEPDMS-4 | 9.35 | PEEPDMS-4 | 3; 9 | 2; 2 |
| PEEPDMS-4 | 9.35 | — | 4; 8 | 3; 3 |
| PEEPDMS-4 | 9.35 | PEEPDMS-4 | 3; 9 | 3; 3 |

The results now show significant reduction of the both dynamic and static friction. No significant influence were found from the container diameter or from surface treatment of the plunger within the studied region which may be due to the relative low molecular weight copolymer. All experiments show increasing static friction by time, this is believed to relate to the liquid-like behaviour of this relative low molecular weight olefin-PDMS block copolymer. Experiments indicate that this increase in static friction can be avoided by using olefin-PDMS block copolymers with higher average molecular weight.

What is claimed is:

1. A coating system for articles having at least a first component and a second component, said second component being in frictional engagement with said first component, wherein at least a part of at least one surface of the component(s) is coated with a silicone oil based coating having a viscosity of at least 200,000 centistokes.

2. A coating system according to claim 1, wherein the coating is applied to a surface of either the first component or the second component.

3. A coating system according to claim 1, wherein the silicone oil is a poly(dialkyl siloxane) oil.

4. A coating system according to claim 3, wherein the poly(dialkyl siloxane) oil is selected from a poly(dimethyl siloxane), poly(dipropyl siloxane) oil poly(dihexyl siloxane) oil.

5. A coating system according to claim 1, wherein the coating comprises a cross-linked silicone oil.

6. A coating system according to claim 5, wherein a part of the silicone oil is not cross-linked.

7. A coating system according to claim 1, wherein the coating comprises a mixture of a cross-linkable silicone oil and a silicone oil which is not cross-linkable.

8. A coating system according to any of claim 1, wherein the coating comprises a block or graft copolymer, or a segmented copolymer based on silicone oil.

9. A coating system according to claim 8, wherein the copolymer forms a laminar structure on the component.

10. A coating system according to claim 8, wherein the block polymer is selected from a diblock, triblock or multiblock copolymer.

11. A coating system according to claim 8, wherein the block copolymer comprises a polyolefinic or polystyrene block.

12. A coating system according to claim 8, wherein the molecular weight of the silicone oil based block is at least 10,000 g/mol.

13. A coating system according to claim 1, wherein the coating on one component comprises a linear or branched oil or a cross-linked oil.

14. A coating system according to claim 1, wherein the thickness of the coating is from 0.005 to 10 $\mu$m.

15. A coating system according to claim 1, wherein the first component is a container made of a material selected from glass, ceramic, metal and plastic.

16. A coating system according to claim 1, wherein the second component is a stopper at least partly made of a flexible material.

17. A coating system according to claim 1, wherein the maximum static friction force between the at least two components after 14 days is below 14 N.

18. A coating system according to claim 1, wherein the maximum dynamic friction force between the at least two components after 14 days is below 12 N.

19. A process of providing a component with a coating material as defined in claim 1, comprising     adding the coating material to the component material prior to molding and subsequently molding the component from the mixture, or     molding the component from the component material and subsequently applying the coating material to the at least one surface of the component.

20. An article having at least a first component and a second component, said second component being in frictional engagement with said first component, wherein at least a part of the surface of the first or the second component is coated with a silicone oil based coating as defined in claim 1.

* * * * *